US009004686B2

(12) United States Patent  
Hirose

(10) Patent No.: US 9,004,686 B2  
(45) Date of Patent: Apr. 14, 2015

(54) IMAGING APPARATUS, CONTROL METHOD, AND STORAGE MEDIUM

(71) Applicant: Canon Kabushiki Kaisha, Tokyo (JP)

(72) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/904,753

(22) Filed: May 29, 2013

(65) Prior Publication Data

US 2013/0321767 A1 Dec. 5, 2013

(30) Foreign Application Priority Data

Jun. 1, 2012 (JP) ................................ 2012-126196

(51) Int. Cl.  
*A61B 3/14* (2006.01)  
*A61B 3/10* (2006.01)  
*A61B 3/00* (2006.01)

(52) U.S. Cl.  
CPC ............. *A61B 3/1025* (2013.01); *A61B 3/0091* (2013.01); *A61B 3/14* (2013.01)

(58) Field of Classification Search  
USPC .................................................. 351/200–246  
See application file for complete search history.

(56) References Cited

U.S. PATENT DOCUMENTS

| 6,337,993 | B1 | 1/2002 | Kishida et al. |
| 6,655,805 | B2 | 12/2003 | Fujieda |
| 7,527,379 | B2 | 5/2009 | Yamaguchi et al. |
| 7,635,186 | B2 | 12/2009 | Kobayashi et al. |
| 7,736,001 | B2 | 6/2010 | Tanaka et al. |
| 8,469,514 | B2 * | 6/2013 | Utsunomiya .................. 351/206 |
| 8,506,081 | B2 | 8/2013 | Matsumoto |
| 8,596,785 | B2 | 12/2013 | Imamura et al. |
| 8,646,915 | B2 * | 2/2014 | Nozato .......................... 351/221 |
| 8,708,489 | B2 * | 4/2014 | Utagawa ....................... 351/206 |
| 2001/0056239 | A1 | 12/2001 | Ono |
| 2007/0216866 | A1 | 9/2007 | Kobayashi et al. |
| 2009/0303428 | A1 | 12/2009 | Tendler |
| 2012/0019780 | A1 | 1/2012 | Nozato |
| 2012/0033180 | A1 | 2/2012 | Pieri et al. |
| 2013/0321765 | A1 | 12/2013 | Yuasa |
| 2013/0321766 | A1 | 12/2013 | Morohashi |
| 2013/0321768 | A1 | 12/2013 | Utagawa |
| 2013/0321769 | A1 | 12/2013 | Kusumoto |

(Continued)

FOREIGN PATENT DOCUMENTS

| JP | 2002-200043 A | 7/2002 |
| JP | 2003-126042 A | 5/2003 |

(Continued)

*Primary Examiner* — Mohammed Hasan  
(74) *Attorney, Agent, or Firm* — Canon U.S.A., Inc. IP Division

(57) ABSTRACT

An imaging apparatus includes a measuring light focusing unit configured to focus measuring light for measuring aberration of an object on the object, an aberration correction unit configured to change a state based on the aberration measured with the measuring light, an imaging light focusing unit configured to focus imaging light for capturing an image of the object on the object, an imaging unit configured to capture an image of the object with the imaging light having passed through the aberration correction unit and the imaging light focusing unit, and a control unit configured to interlockingly control states of the measuring light focusing unit and the imaging light focusing unit.

20 Claims, 12 Drawing Sheets

(56) References Cited

U.S. PATENT DOCUMENTS

2013/0321771 A1 12/2013 Yuasa
2014/0063507 A1 3/2014 Borycki et al.

FOREIGN PATENT DOCUMENTS

| | | |
|---|---|---|
| JP | 2004-033275 A | 2/2004 |
| JP | 2010-259543 A | 11/2010 |

* cited by examiner

IMAGING APPARATUS, CONTROL METHOD, AND STORAGE MEDIUM

BACKGROUND OF THE INVENTION

1. Field of the Invention

The present invention relates to an imaging apparatus that captures an image of an object by radiating imaging light to the object.

2. Description of the Related Art

A scanning laser ophthalmoscope (SLO), which is an ophthalmologic apparatus using a principle of a confocal laser microscope, performs raster scanning for a fundus with a laser that is measuring light, and acquires a planar image from the intensity of its return light with high resolution at a high speed. Concerning the SLO, there has been developed an adaptive optics SLO (AOSLO) apparatus including an adaptive optical system for measuring aberration caused by a subject's eye by a wavefront sensor in real time, and correcting aberration caused by measuring light generated at the subject's eye or its return light. This system enables acquisition of an image reduced in influence of aberration. Japanese Patent Application Laid-Open No. 2010-259543 discusses a composite apparatus that combines an SLO apparatus, which has a wide angle of view, with an AOSLO apparatus, which has a narrow angle of view and high resolution.

SUMMARY OF THE INVENTION

According to an aspect of the present invention, an imaging apparatus includes a measuring light focusing unit configured to focus measuring light for measuring aberration of an object on the object, an aberration correction unit configured to change a state based on the aberration measured with the measuring light, an imaging light focusing unit configured to focus imaging light for capturing an image of the object on the object, an imaging unit configured to capture an image of the object with the imaging light having passed through the aberration correction unit and the imaging light focusing unit, and a control unit configured to interlockingly control states of the measuring light focusing unit and the imaging light focusing unit.

Further features the present invention will become apparent from the following description of exemplary embodiments with reference to the attached drawings.

BRIEF DESCRIPTION OF THE DRAWINGS

FIG. 1A being a top view of the imaging apparatus, and FIG. 1B being a side view of the imaging apparatus.

DESCRIPTION OF THE EMBODIMENTS

Figure 1A:
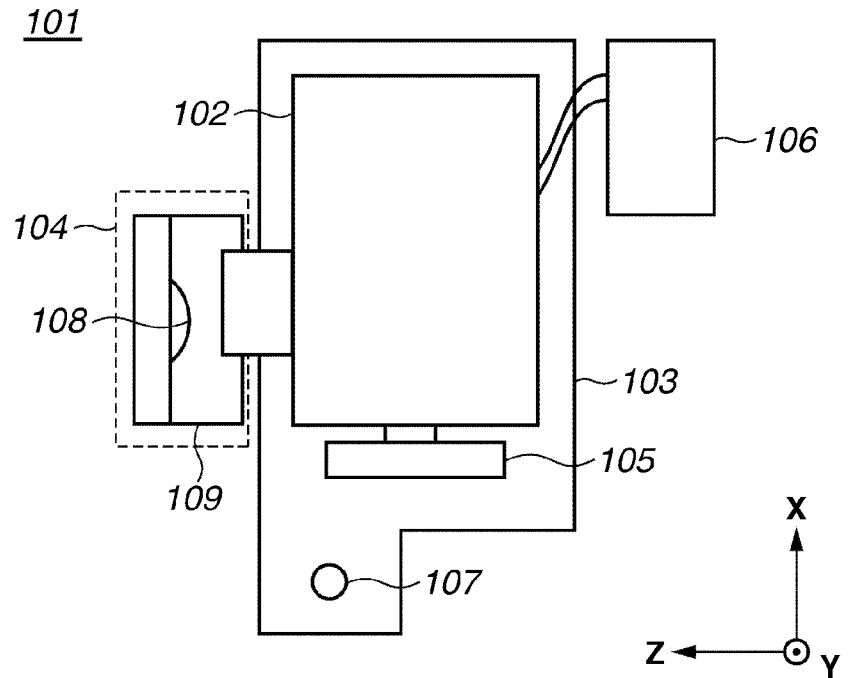
FIGS. 1A and 1B illustrate an appearance configuration of an imaging apparatus according to an exemplary embodiment.

In the case of imaging performed in an AOSLO apparatus that can acquire high-definition images, there is a possibility that a value of aberration may vary between the time of aberration measurement and the time of imaging. It is, therefore, desirable to shorten adjustment before the imaging.

In this case, individually focusing measuring light for aberration measurement and imaging light for imaging on an object may create a possibility of time and labor.

An imaging apparatus according to the present exemplary embodiment includes a measuring light focusing unit (e.g., a measuring light focusing lens movable along an optical axis of an optical path of measuring light) configured to focus the measuring light for measuring aberration of an object on the object, an aberration correction unit configured to change a state thereof based on the aberration measured with the measuring light, an imaging light focusing unit (e.g., an imaging light focusing lens movable along an optical axis of an optical path of imaging light) configured to focus the imaging light for capturing an image of the object on the object, an imaging unit configured to capture an image of the object with the imaging light having passed through the aberration correction unit and the imaging light focusing unit, and a control unit configured to interlockingly control states of the measuring light focusing unit and the imaging light focusing unit (e.g., interlockingly moving the measuring light focusing lens and the imaging light focusing lens).

Thus, image capturing of the object can be quickly performed by an AOSLO apparatus.

Exemplary embodiments of the present invention will be described with reference to the attached drawings.

The AOSLO apparatus according to the exemplary embodiment of the present invention will be described.

The AOSLO apparatus according to the present exemplary embodiment, which includes an adaptive optical system, captures a high lateral resolution planar image (AOSLO image) of a fundus. The apparatus includes a focus lens 217-3 constituting a measuring light focusing unit configured to focus measuring light 206-3 for measuring aberration of the object on the object, and a spatial light modulator 259 constituting an aberration correction unit configured to change a state based on the aberration measured with the measuring light. The apparatus further includes a focus lens 217-1 constituting an imaging light focusing unit configured to focus imaging light for capturing the image of the object on the object, and a detector 238-1 for capturing the image of the object by the imaging light 206-1 passed through the spatial light modulator 259 and the focus lens 217-1. The apparatus also includes a control personal computer (PC) 106 constituting a control unit configured to interlock states of the focus lens 217-3 of the measuring light 206-3 and the focus lens 217-1 of the imaging light 206-1.

For the purpose of assisting the acquisition of the AOSLO image, the AOSLO apparatus can include a WFSLO unit for capturing a wide field angle planar image (WFSLO image), an anterior segment observation unit for recognizing an incident position of imaging light, and a fixation lamp display unit for guiding a line of sight to adjust an imaging place.

In the present exemplary embodiment, the spatial light modulator is used as the adaptive optical system, and the planar image can be acquired by correcting optical aberration caused by a subject's eye. Thus, a good planar image can be acquired irrespective of a diopter of the subject's eye or the optical aberration caused by the subject's eye.

In the present exemplary embodiment, the AOSLO apparatus includes the adaptive optical system to capture a high lateral resolution planar image. However, the adaptive optical system is unnecessary as long as the configuration of the optical system can realize high resolution.

<Overall Configuration of Apparatus>

Figure 1B:
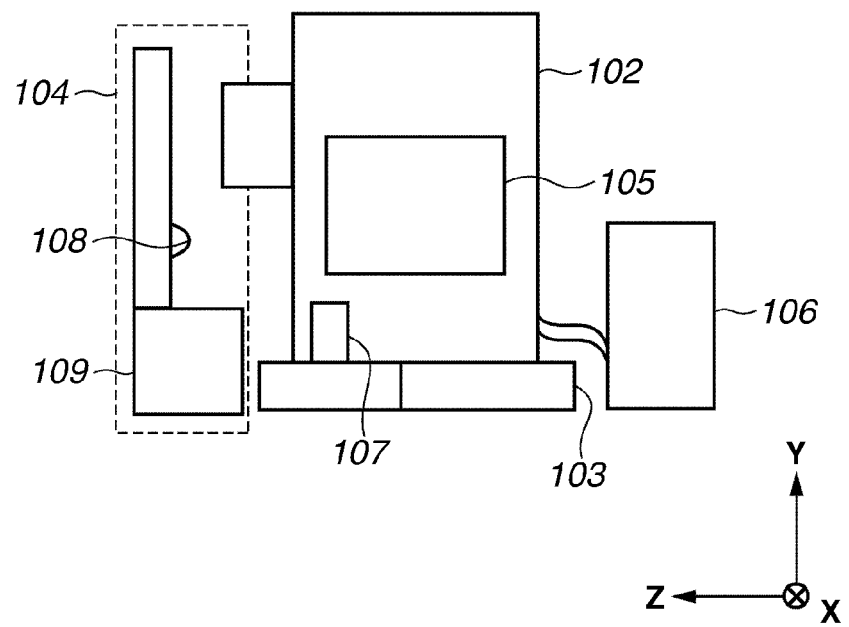

Referring to FIGS. 1A and 1B, an appearance configuration of the AOSLO apparatus 101 according to the present exemplary embodiment will be described. FIG. 1A is a top view of the AOSLO apparatus 101 seen from the upper side, and FIG. 1B is a side view of the AOSLO apparatus 101 seen from the side face.

The AOSLO apparatus 101 includes a light source for measuring aberration, a head unit (measurement unit) 102 including an optical system such as a light source for AOSLO imaging or a focus lens, a stage unit 103 for moving the head unit 102 horizontally or vertically, a face receiver 104 for adjusting a mounting position of a subject's face, a liquid crystal monitor 105 for displaying an operation screen, and the control PC 106 for controlling the entire AOSLO apparatus 101.

The head unit 102 of the AOSLO apparatus 101 includes a focus lens 235-16, a wavefront sensor 255, a spatial light modulator 259, a light source 201-1, a light source 201-2, a focus lens 235-10, a focus lens 235-14, a detector 238-1, a detector 128-2, and a housing for storing these components. The head unit 102, which is installed on the stage unit 103, is horizontally rotated by dropping a joystick 107 so that it can be vertically moved. The face receiver 104 includes a jaw receiver 108 (adjustment unit) on which a jaw is mounted, and a jaw receiver stage unit 109 for moving the jaw receiver 108 horizontally, vertically, or back and forth.

The stage unit 103 constitutes a changing unit for changing a position of the head unit (measurement unit) 102 with respect to the object. The control PC 106 detects and controls an operation amount of the joystick. The jaw receiver stage unit 109 moves a head of the subject detected by the control PC 106 back and forth to secure a focus position, and performs fine adjustment for alignment after the measuring light and the subject's eye have been aligned with each other at the stage unit 103.

The control PC 106 acquires and stores information about the subject in a database in the control PC or an external database through communication from the outside.

<Configuration of Optical System>

Figure 2:
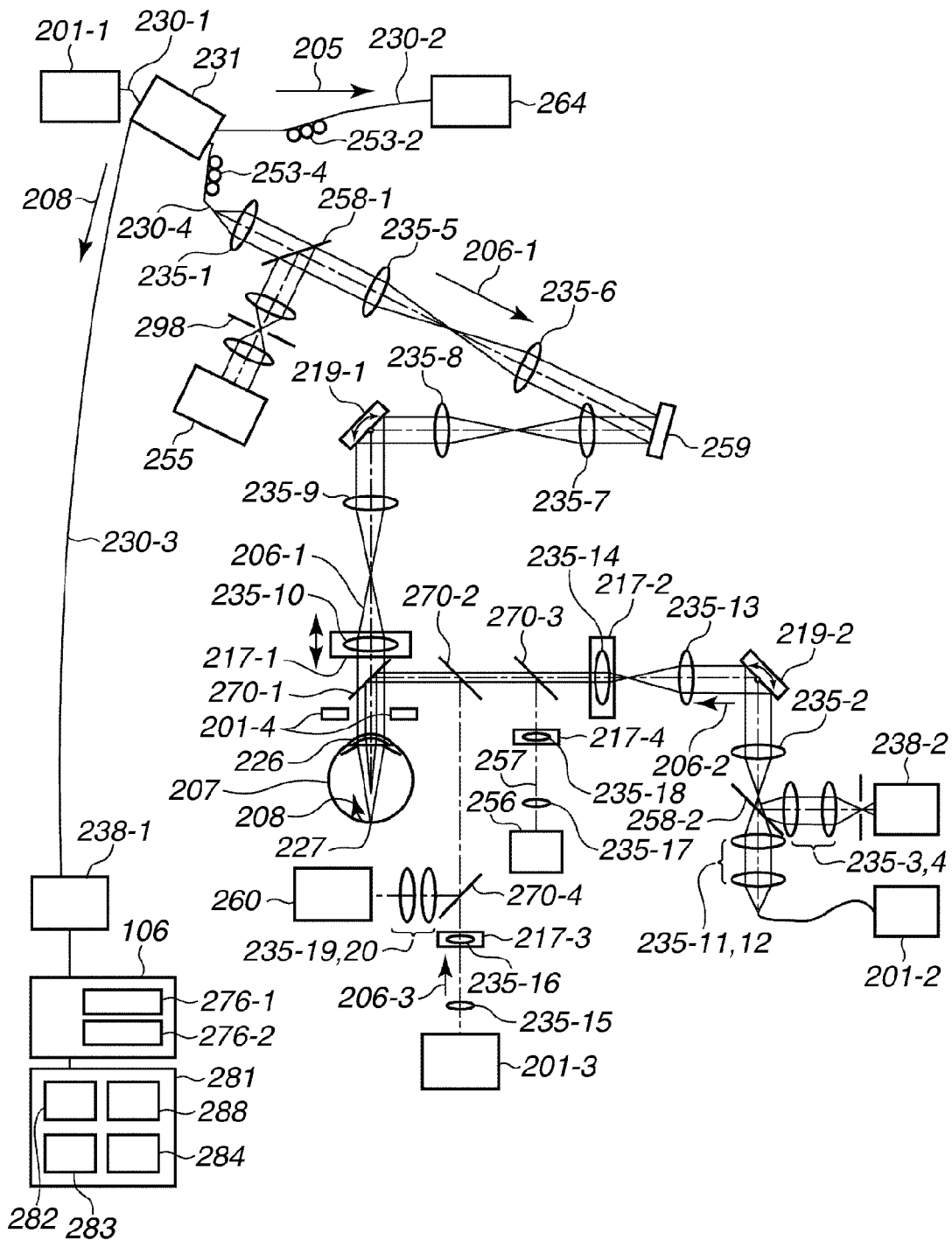
FIG. 2 illustrates a configuration of an optical system of the imaging apparatus according to the exemplary embodiment.

Next referring to FIG. 2, the optical system included in the head unit 102 will specifically be described.

Light emitted from the light source 201-1 is divided into reference light 205 and imaging light 206-1 by a photocoupler 231. The imaging light 206-1 is guided to a subject's eye 207 that is an observation target via a single mode fiber 230-4, the spatial light modulator 259, an XY scanner 219-1, and a dichroic mirror 270-1. The passage through the spatial light modulator enables acquisition of an image reduced in aberration.

Alight flux 257 from a fixation lamp 256 plays a role of prompting fixation or rotation of the subject's eye 207.

The imaging light 206-1, which is converted into reflected or scattered light 208 by the subject's eye 207, reversely travels on an optical path, and enters the detector 238-1 via the photocoupler 231. The detector 238-1 converts the intensity of the return light 208 into a voltage, and a planar image of the subject's eye 207 is formed by using its signal. In the present exemplary embodiment, the entire optical system is configured by using a refractive optical system mainly using a lens. However, the optical system can be configured by a reflective optical system using a spherical mirror in place of the lens.

In the present exemplary embodiment, the reflective spatial light modulator is used as an aberration correction device. However, a transmissive spatial light modulator or a variable-shape mirror can be used.

<Light Source of AOSLO Unit>

Next, a portion around the light source 201-1 will be described. The light source 201-1 is a super luminescent diode (SLD), which is a representative low-coherent light source. A wavelength is 840 nm, and a bandwidth is 50 nm. In this case, the low-coherent light source is used to acquire a planar image having limited speckle noise. Any type of a light source can be used as long as it can emit low-coherent light while the SLD is selected, and an amplified spontaneous emission (ASE) or the like can be used.

For the wavelength, near-infrared light is suitable in view of eye measurement. Further, a shorter wavelength is desirable because it affects horizontal resolution of the acquired planar image and, in this case, the wavelength is 840 nm. Other wavelengths can be selected depending on measured portions of the observation target.

The light emitted from the light source 201-1 is divided into the reference light 205 and the imaging light 206-1 at a rate of 90:10 via the single mode fiber 230-1 and the photocoupler 231. The AOSLO apparatus includes a polarization controller 253.

<Reference Optical Path of AOSLO Unit>

Next, an optical path of the reference light 205 will be described.

The reference light 205 divided by the photocoupler 231 enters a light amount measurement apparatus 264 via an optical fiber 230-2. The light amount measurement apparatus 264 is used for measuring an amount of the reference light 205 and monitoring an amount of the imaging light 206-1.

<Imaging Optical Path of AOSLO Unit>

Next, an optical path of the imaging light 206-1 will be described.

The imaging light 206-1 divided by the photocoupler 231 is guided to a lens 235-1 via a single mode fiber 230-4, and adjusted to be parallel light having a diameter of 4 mm.

The imaging light 206-1 passes through a beam splitter 258-1 and lenses 235-5 and 235-6 to enter the spatial light modulator 259.

Then, the imaging light 206-1 is modulated by the spatial light modulator 259, and passes through lenses 235-7 and 235-8 to enter into the XY scanner 219-1. For simplicity, the XY scanner 219-1 is a single mirror. In reality, however, two mirrors are arranged close to each other as an X scanner and a Y scanner, and raster scanning is performed on a retina 227 vertically to the optical axis. A center of the imaging light 206-1 is adjusted to coincide with a mirror rotational center of the XY scanner 219-1.

The X scanner scans the imaging light 206-1 in a direction parallel to a paper surface, and a resonance scanner is used. A driving frequency is about 7.9 kHz. The Y scanner scans the imaging light 206-1 in a direction vertical to the paper surface, and a Galvano scanner is used. A driving waveform is a saw-tooth wave, a frequency is about 32 Hz, and a duty ratio is 16%. The driving frequency of the Y scanner is an important parameter for determining a frame rate of a captured AOSLO image.

The XY scanner 219-1 is controlled by the control PC 106 via an optical scanner driver 282 in a driver unit 281.

The lenses 235-9 and 235-10, which are optical systems for scanning the retina 227, play roles of scanning the retina 227 with the imaging light 206-1 with a pupil center of the subject's eye 207 set as a supporting point.

A diameter of the imaging light 206-1 is 4 mm. However, the beam diameter can be larger to acquire an optical image of higher resolution.

An electric stage 217-1 can be moved in an arrow direction illustrated in FIG. 2, i.e., an optical axis direction. A position of the focus lens 235-10 fixed to the electric stage 217-1 is accordingly moved to adjust a focus. Thus, the focus lens 235-10 and the electric stage 217-1 constitute a focusing unit (focusing unit) for focusing the imaging light of the AOSLO on the object. The electric stage 217-1 is controlled by the control PC (control apparatus or control unit) 106 via an electric stage driver 283 in the driver unit 281. Adjusting the position of the lens 235-10 enables focusing of the imaging light 206-1 at a position in a specific depth direction in the retina 227 of the subject's eye 207. The apparatus can even deal with refraction abnormality in the subject's eye 207.

Since the imaging light needs to be focused for a position of the imaging target of the fundus, a focusing position is determined according to the position of the imaging target of the fundus in addition to aberration caused by the apparatus and a dipoter value of the subject's eye. The focusing position can be set manually by a user interface (UI) described below. However, for example, if the focusing position can be automatically set by disposing a dedicated focus sensor, the adjustment step can be shortened. Further, by using a luminance value or a statistical value of an image acquired by an imaging optical system (WFSLO) different from the AOSLO as illustrated in FIG. 2, automatic focus control can be performed without any dedicated focus lens.

The imaging light 206-1, which has entered into the subject's eye 207, is converted into return light 208 by reflection or scattering from the retina 227 to be guided to the optical coupler 232 again, and reaches the detector 238-1 via the single mode fiber 230-3. For the detector 238-1, for example, an avalanche photodiode (APD) or a photomultiplier tube (PMT) that is a high-speed and high-sensitivity optical sensor is used. The detector 238-1 constitutes an imaging unit for detecting the return light of the imaging light from the object via the spatial light modulator and the imaging light focusing unit to capture an image of the object.

<Beacon (Aberration Measurement) Unit and Aberration Correction Unit>

Next, a beacon (aberration measurement) unit that measures aberration generated in the subject's eye 207 will be described.

Measuring light 206-3 emitted from the light source 201-3 is guided to the subject's eye 207, which is an observation target, via lenses 235-15 and 235-16, and a dichroic mirror 270-4. A part of the return light 208 from the subject's eye 207 is radiated to the wavefront sensor 255 via a dichroic mirror 258-1 and a pinhole 298, and aberration of the return light 208 generated in the subject's eye is measured.

An electric stage 217-3 can be moved in the arrow direction illustrated in FIG. 2, i.e., the optical axis direction. A position of the focus lens 235-16 fixed to the electric stage 217-3 is accordingly moved to adjust a focus. Thus, the focus lens 235-16 and the electric stage 217-3 function as a focusing unit for focusing the measuring light 206-3 for measuring the aberration on the object. As in the case of the focus lens 217-1 of the AOSLO, the electric stage 217-3 is controlled by the control PC (control apparatus or control unit) 106 via the electric stage driver 283 in the driver unit 281.

The measuring light, which only needs to be focused on the fundus, is determined according to a diopter value of the subject's eye except for aberration caused by the apparatus.

The wavefront sensor 255 constitutes an aberration measurement unit that detects measuring light to measure aberration in the optical path. The wavefront sensor 255 is electrically connected to the control PC 106. The wavefront sensor 255 is a Shack-Hartman wavefront sensor, and a measurement range is −10D to +5D. The acquired aberration is expressed by using Zernike polynomial, which indicates aberration at the subject's eye 207. The Zernike polynomial includes a tilt term, a defocus term, an astigmatism term, a coma term, and a trefoil term. A center wavelength of the light source 201-3 is 760 nm, and a wavelength width is 20 nm.

The measuring light 206-3 is, to prevent reflection from a cornea 226, deviated from a center of the subject's eye 207 to enter. This will be described below referring to FIGS. 1A and 1B, and FIG. 2. The pinhole 298 is installed to block out unnecessary light other than the return light 208, and the return light of the measuring light having passed through the pinhole 298 is detected by the wavefront sensor 255. This can reduce a possibility of detection of light not passing through the fundus of the subject's eye, and thus the aberration can be accurately measured. Further, by disposing the focusing unit of the measuring light, the measuring light appropriately passes through the pinhole 298, and thus the aberration can be accurately measured.

The lenses 135-5 to 235-10 are arranged so that the cornea 226, the XY scanner 219-1, the wavefront sensor 255, and the spatial light modulator 259 can be optically conjugate with one another. Thus, the wavefront sensor 255 can measure the aberration caused by the subject's eye 207.

The spatial light modulator 259 functions as an aberration correction unit that corrects the aberration caused by the subject's eye 207 or the optical system of the apparatus. For example, the spatial light modulator 259, which can modulate a phase of the light by a liquid crystal, compensates for the aberration by canceling the measured aberration. The spatial light modulator 259 is controlled for its state by the control PC 106 via a spatial light modulator driver 288 in the driver unit 281. Accordingly, the imaging light 206-1 and its return light form images on an incident surface of the detector 238-1 in the state where the aberration in the optical path has been compensated for to be reduced. The detector 238-1 detects the return light reduced in influence of aberration, and the image of the object can be captured.

The control PC 106 interlockingly controls the states of the focus lens 235-14 for the measuring light 206-3 and the focus lens 235-10 for the imaging light 206-1 of the AOSLO. The focus position changes depending on the diopter of the subject. However, correspondence can be set between the positions of the focus lenses by taking into consideration the optical system of the aberration measurement and the imaging optical system of the AOSLO. In other words, if one light can be focused according to the diopter of the subject, the position of the other focus lens corresponding to the position of one focus lens is uniquely determined. The correspondence between the states of the focus lenses is stored in the storage unit and, by referring to it as occasion demands, the other focus lens can be adjusted according to adjustment of one focus lens. As a result, time and labor of the adjustment step of imaging preparation can be reduced compared with the case of individual adjustment.

Further, a value of the aberration calculated according to an output from the wavefront sensor 255 functioning as the aberration measurement unit includes a defocus value as described above. The control PC 106 can further control the position of the focus lens 235-10 of the AOSLO according to the defocus value. This two-stage adjustment enables fine adjustment of the focus lens of the AOSLO, which needs more detailed adjustment.

<Entire WFSLO Unit>

The AOSLO apparatus 101 can include a WFSLO unit to capture an image having a field angle wider than that of the AOSLO. Hereinafter, the WFSLO unit will be described.

The WFSLO unit has a configuration basically similar to that of the AOSLO unit. Description of overlapped portions will be omitted.

Imaging light (WFSLO imaging light) emitted from the light source (second imaging light source) 201-2 is guided to the subject's eye 207, which is an observation target, via the lens 235-2, the lenses 235-11 to 235-14, the XY scanner 219-2, and the dichroic mirrors 270-1 to 270-3. The light source 201-2 is an SLD as in the case of the AOSLO unit. A wavelength is 920 nm, and a band width is 20 nm.

<Imaging Optical Path of WFSLO Unit>

Next, an optical path of the imaging light 206-2 will be described.

The imaging light 206-2 emitted from the light source 201-2 is guided to the subject's eye 207, which is an observation target, via the lens 235-2, the lenses 235-11 to 235-14, the XY scanner 219-2, and the dichroic mirror 270-1.

The X scanner, which is a component of the XY scanner 219-2, scans the imaging light 206-2 in a direction parallel to a paper surface, and a resonance scanner is used. A driving frequency is about 3.9 kHz. The Y scanner scans the imaging light 206-2 in a direction vertical to the paper surface, and a Galvano scanner is used. A driving waveform is a saw-tooth wave, a frequency is 15 Hz, and a duty ratio is 16%. The driving frequency of the Y scanner is an important parameter for determining a frame rate of a WFSLO image.

An electric stage 217-2 can be moved in the arrow direction illustrated in FIG. 2, i.e., the optical axis direction. A position of the focus lens 235-14 fixed to the electric stage 217-2 is accordingly moved to adjust a focus. Thus, the focus lens 235-14 and the electric stage 217-2 constitute a focusing unit for focusing the imaging light of the WFSLO on the object. The electric stage 217-2 is controlled by the control PC (control apparatus or control unit) 106 via the electric stage driver 283 in the driver unit 281.

A diameter of the imaging light 206-2 is 1 mm. However, the beam diameter can be larger to acquire an optical image of higher resolution.

The imaging beam 206-2, which has entered the subject's eye 207, is converted into return light 208 by reflection or scattering from the retina 227, and reaches the detector 238-2 via the dichroic mirrors 270-1 to 270-3, the lenses 235-13 to 235-14, the lenses 235-2 to 235-4, the XY scanner 219-2, and the beam splitter 258-2. The detector 238-2 constitutes an imaging unit for detecting the imaging light 206-2 of the WFSLO to capture an image having a field angle wider than that of the AOSLO image.

The control PC 106 interlockingly controls the focus lens 234-10 of the imaging light 206-1 of the AOSLO, the focus lens 235-16 of the beacon light (measuring light) 206-3, and the focus lens 235-14 of the imaging light 206-2 of the WFSLO. The focus positions of all the focus lenses change depending on the diopter of the subject. However, since other conditions are almost fixed, the position of the other focus lens corresponding to the position of one focus lens can be determined. Thus, focusing with the AOSLO, the measuring light of the aberration, and the WFSLO can be easily controlled.

<Fixation Lamp>

Figure 7:
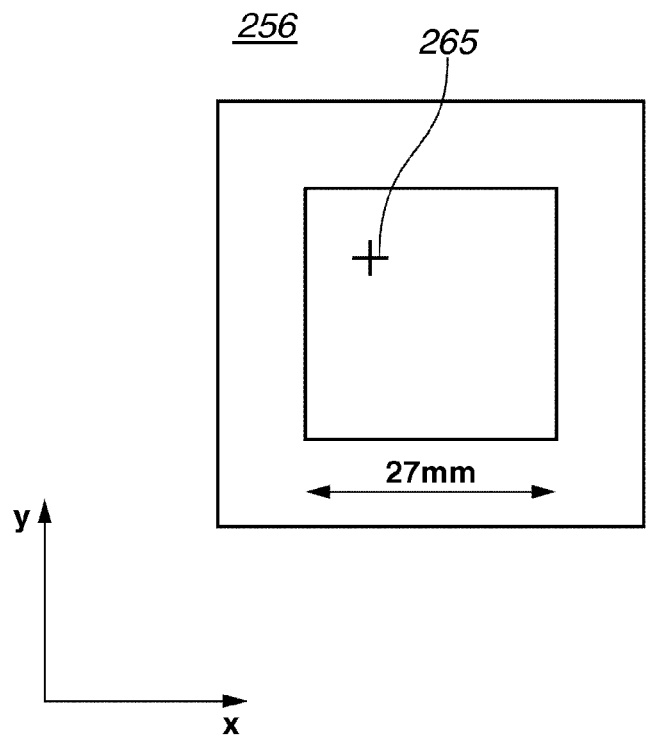
FIG. 7 illustrates a display screen of a fixation lamp according to the exemplary embodiment.

The AOSLO apparatus 101 can include a fixation lamp for fixating the subject's eye. The fixation lamp 256, which includes a light emitting display module, has a display surface (27 mm, 128×128 pixels) on an XY plane. A liquid crystal, an organic electroluminescence (EL), or a light emitting diode (LED) array can be used. The subject's eye 207 pays close attention to a light flux 257 from the fixation lamp 256, and accordingly fixation or rotation of the subject's eye 207 is prompted. In the display surface of the fixation lamp 256, for example, as illustrated in FIG. 7, a cross pattern is flashed to be displayed at an arbitrary lighting position 265.

The light flux 257 from the fixation lamp 256 is guided to the retina 227 via the lenses 235-17 and 18 and dichroic mirrors 270-1 to 270-3. The lenses 235-17 and 235-18 are arranged so that the display surface of the fixation lamp 256 and the retina 227 can be optically conjugate with each other. The fixation lamp 256 is controlled by the control PC 106 via a fixation lamp driver 284 in the driver unit 281.

An electric stage 217-4 can be moved in the arrow direction illustrated in FIG. 2, i.e., the optical axis direction. A position of the focus lens 235-18 fixed to the electric stage 217-4 is accordingly moved to adjust a focus. Thus, the focus lens 235-18 and the electric stage 217-4 constitute a focusing unit for focusing a fixation target of the fixation lamp on the object. The electric stage 217-4 is controlled by the control PC (control apparatus or control unit) 106 via the electric stage driver 283 in the driver unit 281.

The control PC 106 interlockingly controls the focus lens 234-10 for the imaging light 206-1 of the AOSLO, the focus lens 235-16 for the beacon light (measuring light) 206-3, the focus lens 235-14 for the imaging light 206-2 of the WFSLO, and the focus lens 235-18 for the fixation lamp. Thus, focusing with the AOSLO, the measuring light of the aberration, the WFSLO, and the fixation lamp can be easily controlled.

<Anterior Segment Observation Unit>

Next, the anterior segment observation unit will be described.

Light emitted from the anterior segment observation unit 201-4 illuminates the subject's eye 207, and its reflected light enters a charge-coupled device (CCD) camera 260 via the dichroic mirrors 207-1, 207-2, and 207-4 and lenses 235-19 and 235-20. The light source 201-4 is an LED having a center wavelength of 740 nm.

<Focus, Shutter, and Astigmatism Correction>

As described above, the optical system in the head unit 102 includes the AOSLO unit, the WFSLO unit, the beacon unit, the fixation lamp unit, and the anterior segment observation unit. The AOSLO unit, the WFSLO unit, the beacon unit, and the fixation lamp unit individually include the electric stages 217-1 to 217-4, and the four electric stages are interlockingly operated. However, when focus positions are individually adjusted, the positions can be adjusted by individually operating the electric stages.

Especially, the focus lenses of the WFSLO unit, the beacon unit, and the fixation lamp other than the AOSLO can be interlocked because their positions change depending on the diopter of the subject's eye. However, for the AOSLO, the position of the focus lens changes depending on, in addition to the diopter, an imaging position of the subject's eye, which is an imaging target, in a depth direction. Thus, for the focus lens 235-10 of the AOSLO, a position can be changed independently of the other focus lenses under control of the control PC 106.

Each of the AOSLO unit, the WFSLO unit, and the beacon unit includes a shutter (not illustrated), and whether to allow light to enter the subject's eye 207 can be individually controlled by opening or closing the shutter. In this case, the shutter is used. However, control can be performed by directly turning ON/OFF the light sources 201-1 to 201-3. Similarly, the anterior segment observation unit and the fixation lamp unit can be controlled by turning ON/OFF the light source 201-4 and the fixation lamp 256.

The lens 235-10 can be replaceable, and a spherical lens or a cylindrical lens can be used according to the aberration (refraction abnormality) caused by the subject's eye 207. Not limited to one lens, a plurality of lenses can be combined to be installed.

<Wavelength>

Figure 3:
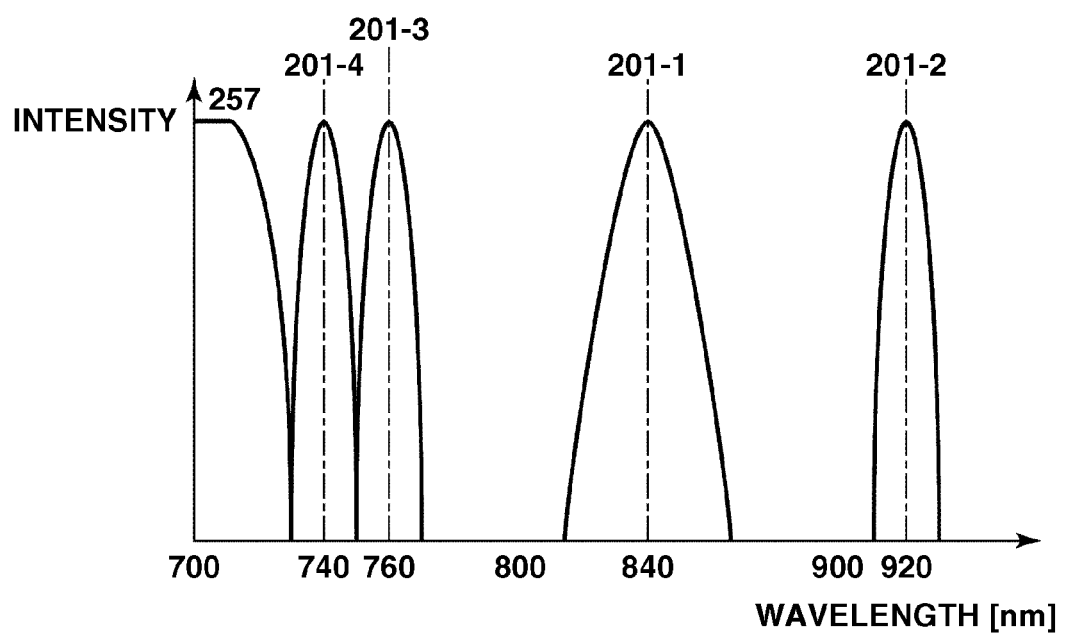
FIG. 3 illustrates a wavelength distribution of light used in an AOSLO apparatus.

FIG. 3 illustrates a wavelength distribution of the light sources used for the AOSLO unit, the WFSLO unit, the beacon unit, the fixation lamp unit, and the anterior segment observation unit. The light beams are divided by the dichroic mirrors 270-1 to 270-4, and thus have different wavelength ranges. FIG. 3, which illustrates a difference in wavelength among the light sources, does not define the intensity or spectral shapes thereof.

<Image Formation>

Next, a configuration method of a captured mage will be described.

For the light entering the detector 238-1, its intensity is converted into a voltage. A voltage signal acquired at the detector 238-1 is converted into a digital value at an AD board 276-1 in the control PC 106. The control PC 106 performs data processing in synchronization with an operation or a driving frequency of the XY scanner 219-1 to form an AOSLO image. A capturing speed of the AD board 276-1 is 15 MHz. Similarly, a voltage signal acquired at the detector 238-2 is converted into a digital value at an AD board 276-2 in the control PC 106, and a WFSLO image is formed.

<Details on Control PC>

Figure 4:
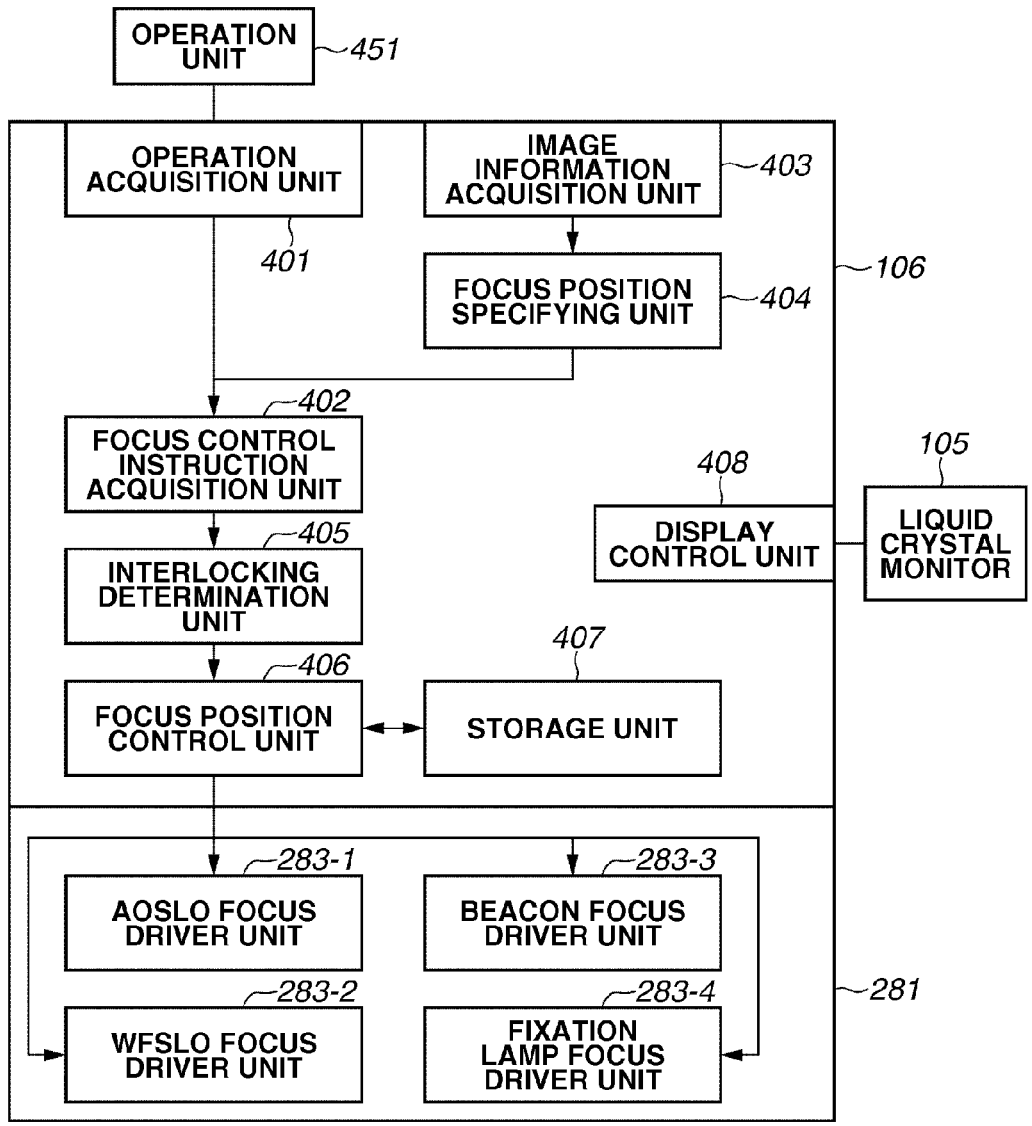
FIG. 4 illustrates a configuration of a control apparatus according to the exemplary embodiment.

Referring to FIG. 4, a configuration concerning focus control of the control PC 106 will be described. The control PC includes an operation acquisition unit 401, a focus control instruction acquisition unit 402, an information acquisition unit 403, a focus position specifying unit 404, an interlocking determination unit 405, a focus position control unit 406, a storage unit 407, and a display control unit 408. The control PC 106 is connected to the driver unit 281, an operation unit 451, and a liquid crystal monitor 105. The driver unit 281 includes, as focus driver units, an AOSLO focus driver unit 283-1, a WFSLO focus driver unit 283-2, a beacon focus driver unit 283-3, and a fixation lamp focus driver unit 283-4.

The operation acquisition unit 401 acquires an operation input from the operation unit 451. The operation acquisition unit 401 includes, for example, a graphical user interface (GUI) described below, or an operation device or a touch panel for operating the GUI illustrated in FIG. 5.

The focus control instruction acquisition unit 402 acquires, among the operation inputs acquired by the operation acquisition unit 401, an input concerning focus adjustment. For example, when there is an input of operating the GUI button for focus adjustment, an input value is acquired.

Focus control instruction includes not only manual control instruction but also control instruction issued in response to a command from the apparatus. For example, the control PC 106 can include the information acquisition unit 403 and the focus position specifying unit 404. The focus position specifying unit 404 specifies a position to which the focus lens is moved. The position to which the focus lens is moved includes a case where the position of the focus lens for searching to specify a focusing position is moved and a case where a focusing position is specified according to an input from the outside.

In the case of searching, the information acquisition unit 403 acquires an image by, for example, the WFSLO while moving the focus lens with an appropriate moving width. The focus position specifying unit 404 specifies an optimal or quasi-optimal focusing position by using a contrast or luminance value of an image or a statistical value of the luminance value. The specified position information is notified to the focus control instruction acquisition unit 402. Alternatively, a vector value defined based on a moving amount or direction of the focus lens can be notified to the focus control instruction acquisition unit 402.

In the case of specifying the focus position according to the input from the outside, the focus position specifying unit 404, which has received an input from the focus sensor, specifies the focusing position, and notifies a vector value to move the focus lens based on the specified position information to the focus control instruction acquisition unit 402.

In yet another case, the focus lens is moved according to a default value from the wavefront sensor 255. In this case, the information acquisition unit 403 acquires the default value, and the focus position specifying unit 404 specifies a moving amount of the focus lens.

The interlocking determination unit 405 determines whether to interlock a plurality of focus lenses. For example, when the focus of the AOSLO is moved to determine an imaging position, movement of the other focus lenses is not necessary. Information about this is acquired from the focus control instruction acquisition unit 402, and the interlocking determination unit 405 determines control of only the focus of the AOSLO. For example, when there is an input from the GUI to instruct only the focus of the AOSLO, noninterlocking is determined. When there is an input from another GUI, interlocking is determined.

In the case of starting adjustment for imaging, interlockingly controlling the plurality of focus lenses according to the object is more efficient than individual adjustment. Accordingly, when control instruction of one focus lens is acquired immediately after an alignment end of the subject's eye, the interlocking determination unit 405 determines interlocking of the plurality of focus lenses. In the case of imaging only by the AOSLO not needing imaging by the WFSLO, the interlocking determination unit 405 can determine interlocking of, not the WFSLO alone, the beacon light (measuring light), the fixation lamp, and the focus lens of the AOSLO.

The focus position control unit 406 acquires a lookup table indicating correspondence between the interlocking determination and which focus lens is moved and how much according to the moving amount of one focus lens from the storage unit 407. The focus position control unit 406 calculates a moving amount of each focus lens by referring to the lookup table. In place of the lookup table indicating the correspondence, a function indicating the correspondence can be stored in the storage unit 407, and the moving amount of each focus lens can be calculated by appropriately referring to the function.

The focus position control unit 406 issues instruction about a moving amount, a moving direction, and movement of the focus lens to a necessary unit among the focus drivers 283-1 to 283-4 of the driver unit 281. Accordingly, the focus drivers drive the electric stages 217-1 to 217-4 for moving the corresponding focus lenses.

Thus, according to the instruction of changing the state of one focusing unit, the state of the focusing unit can be changed by determining a corresponding focusing unit to be interlocked and instructing the focus driver. By adaptive determination, the state of an appropriate focusing unit can be changed according to a status. Further, one focusing unit can be individually controlled independently.

Each unit of the control PC 106, which can be configured by using a dedicated circuit, can also be configured by using software and the hardware of the control PC 106. In this case, a central processing unit (CPU) of the control PC 106 can function as each unit illustrated in FIG. 4 by rasterizing programs stored in a read-only memory (ROM) to sequentially execute them, and can execute processing described below referring to FIGS. 8 to 10.

Further, the display control unit 408 can display the GUI illustrated in FIG. 5 and described below on a liquid crystal monitor 105 constituting a display unit. Thus, for example, a user can instruct control of the focus lens from the GUI.

<GUI of Control Software>

Next, referring to FIG. 5, the GUI displayed on the liquid crystal monitor 105 by the display control unit 408 will be described. An execution button 501 is a button for starting imaging of the apparatus. By pressing the button 501, the anterior segment imaging light source 201-4 is lit, and an image detected and captured by the CCD camera 260 is displayed on the anterior segment monitor 512. A stop button 502 is a button for ending the imaging. An electric stage button 503 is a button for moving the jaw receiver, and corresponding buttons are respectively arranged in an X direction, a Y direction, and a Z direction. By pressing the button 503, the jaw receiver driving unit 109 can be finely moved. A button can be disposed to move the head unit 102 in the X, Y, and Z directions.

A focus adjustment button 504 is a button (second instruction unit) for interlockingly moving the focus lens 235-10 of the imaging light 206-1 of the AOSLO, the focus lens 235-16 of the beacon light (measuring light) 206-3, and their focus lenses when a WFSLO and a fixation lamp are present. For example, the focus adjustment button 504 can include a button for moving the focus lens in a first direction and a button for moving the focus lens in a second direction. In response to pressing of the focus adjustment button 504, focus searching can be automatically started.

A WFSLO imaging instruction button 505 is a button for switching ON/OFF of displaying of an image on a WFSLO monitor 515 of the WFSLO image. It can be a button for instructing activation or stop of the scanner or the detector of the WFSLO. Simultaneously with displaying of the image on the WFSLO monitor 515, information indicating the intensity of the WFSLO image is displayed on a WFSLO intensity monitor 516. For example, the signal intensity detected by the WFSLO unit is time-sequentially displayed with a horizontal axis indicating time and a vertical axis indicating the signal intensity. To record the WFSLO image, a recording start is instructed by pressing a WFSLO recording button 517, and a WFSLO moving image is accordingly stored in the storage unit 410. An instruction button for storing a still image or one frame can also be disposed. Further, a button for instructing outputting of one frame to a paper medium by a printer (not illustrated) can be disposed.

If without pressing the WFSLO imaging instruction button 505, WFSLO imaging or image displaying is automatically started according to completion of alignment based on the anterior segment image, operation time and labor can be reduced.

An aberration measurement button 506 is operable for starting emission of the beacon light (measuring light) 206-3, and displaying a Hartman image acquired by the wavefront sensor 255 on a wavefront sensor monitor 514. Aberration calculated from the Hartman image is displayed on an aberration correction monitor 511. The process from the acquisition of the Hartman image to the calculation of the aberration is executed by a module in the wavefront sensor 255. However, the aberration can be calculated from the Harman image by disposing another module. The wavefront sensor 255 sequentially calculates the aberration based on the acquired Hartman image. Thus, when the state of the spatial light modulator 259 is controlled to reduce the aberration, the aberration displayed on the aberration correction monitor 511 varies.

An autofocus button 521 is a button (third instruction button) for adjusting the positions of the focus lenses 235-10, 235-14, 235-16, and 235-18 by using a defocus value acquired by the wavefront sensor 255. In response to pressing of the button, the focus position control unit 406 of the control PC interlockingly controls the four focus lenses.

By pressing an aberration correction button 522, the state of the spatial light modulator 259 is automatically controlled to reduce an aberration amount. For example, if imaging of the AOSLO is instructed when the aberration amount is lower than a specific threshold value, operation time and labor are reduced, and quick imaging can be performed.

An aberration correction temporary stop button 508 is a button for temporarily stopping searching for aberration correction when the aberration is not automatically reduced to an appropriate value after the aberration measurement button 506 is pressed.

An AOSLO measurement button 507 is a button for instructing an imaging start of the AOSLO. It can be a button for instructing a displaying start of an image captured by the AOSLO. Accordingly, the shutter of the AOSLO 206-1 is opened, the imaging light 206-1 is radiated to the object, and an AOSLO image reduced in aberration is displayed on an AOSLO intensity monitor 518. Information indicating the signal intensity detected by the detector 238-1 is displayed on an AOSLO intensity monitor 519. For this information, as in the case of the information displayed on the WFSLO intensity monitor 516, the signal intensity detected by the WFSLO unit is time-sequentially displayed with a horizontal axis indicating time and a vertical axis indicating the signal intensity.

A depth adjustment button 524 is a button (first instruction unit) for controlling the focus lens 235-10 of the AOSLO independently of the other focus lenses. The depth adjustment button 524 includes buttons for respectively moving the focus lenses in a first direction and a second direction. In response to pressing of each button, the focus position control unit 406 of the control PC 106 changes the position of the focus lens 235-10. Thus, the imaging position of the AOSLO in the depth direction can changed.

An AOSLO recording button 520 is a button for instructing a recording start or end of the AOSLO. A moving image of the AOSLO acquired during the period from the instruction of the recording start to the instruction of the recording end is stored in the storage unit 407.

A fixation lamp position monitor 513 displays a position of the fixation lamp.

An operation condition setting button 523 is a GUI for designating an imaging range, a frame rate, and imaging time. Appropriate imaging conditions can be input.

Figure 5:
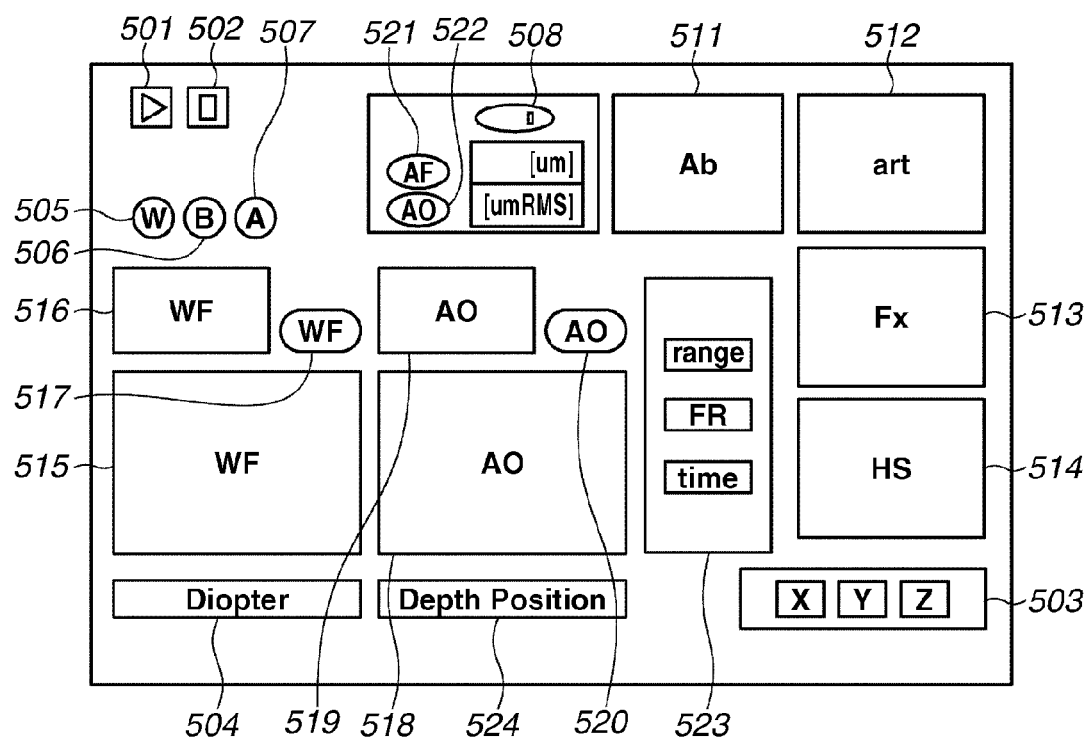
FIG. 5 illustrates a control software screen according to the exemplary embodiment.

Thus, inputs from the buttons arranged in the GUI illustrated in FIG. 5 are all received by the control PC 106, and each unit of the AOSLO apparatus is controlled according to the input.

<Checking of Image>

Next, referring to FIG. 6, a method for forming an image of data captured in the AOSLO apparatus of the present exemplary embodiment and checking it will be described.

Figure 6:
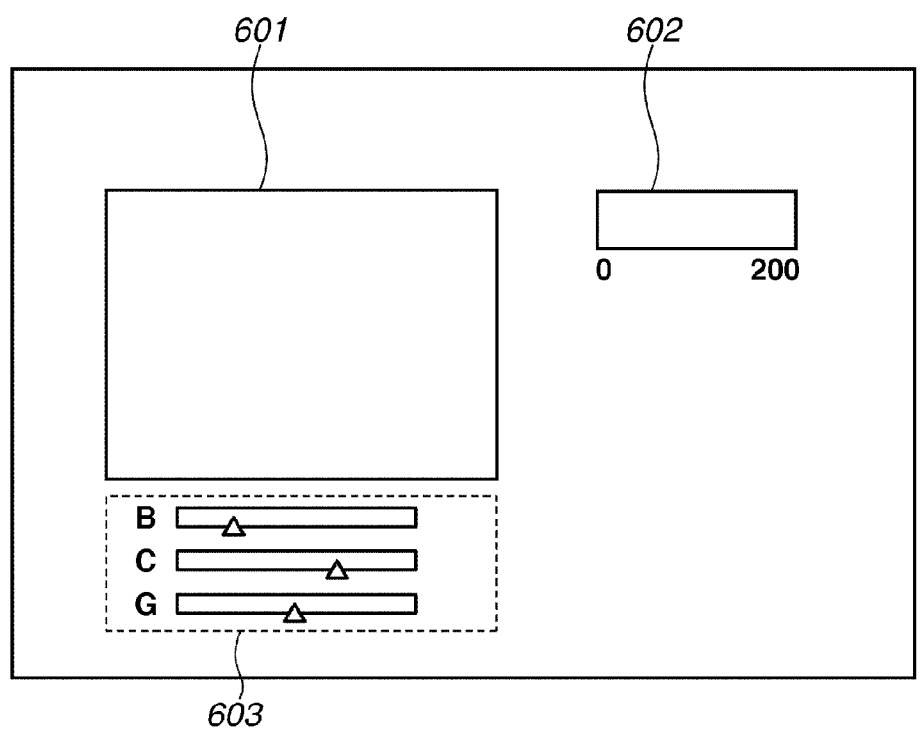
FIG. 6 illustrates an image viewing software screen according to the exemplary embodiment.

When viewer software for making the captured image data visible is activated, a viewer software screen illustrated in FIG. 6 is displayed on the liquid crystal monitor 105.

The stored WFSLO image or AOSLO image can be read to be formed into an image.

The number of images to be captured varies depending on measuring time, and image numbers are added in order of time. An image having an image number designated by an image number selection unit 602 is displayed on an image display unit 601. An image quality adjustment unit 603 includes knobs for adjusting image brightness, contrast, and gamma. Image quality can be adjusted by sliding the knobs left and right.

<Imaging Procedure>

Next, referring to FIGS. 5 and 8, an imaging procedure in the AOSLO apparatus of the present exemplary embodiment will be described.

Figure 8:
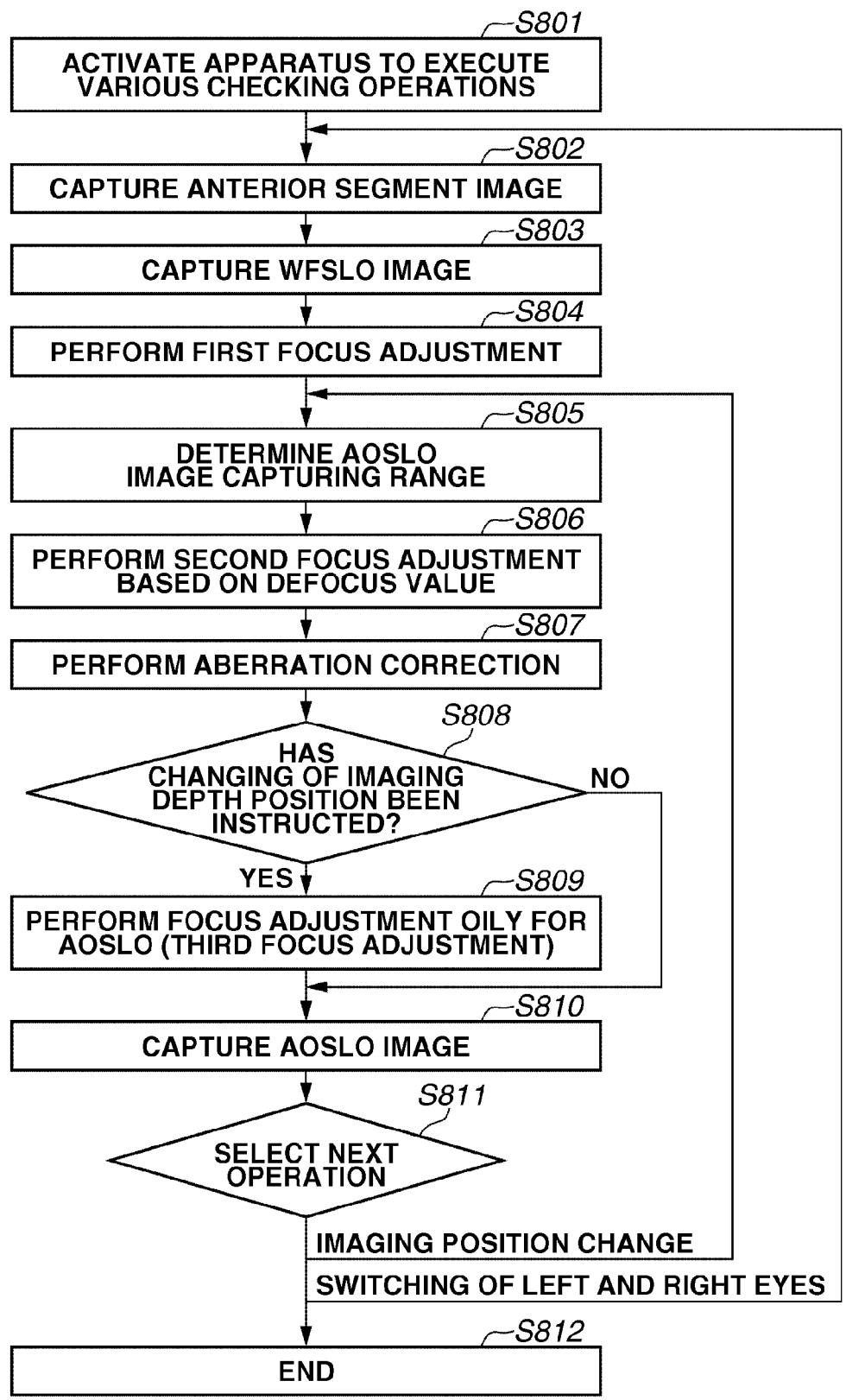
FIG. 8 is a flowchart illustrating an imaging procedure by an SLO apparatus according to the exemplary embodiment.

FIG. 8 illustrates the imaging procedure. Hereinafter, each step will be described in detail.

In step S801, the apparatus is activated to perform various checking operations. Power is turned ON for the control PC 106 and the AOSLO apparatus. Then, the measurement control software is activated to display the control software screen illustrated in FIG. 5 on the liquid crystal monitor 105. The subject sets the face on the face receiver 104.

In step S802, an anterior segment image is captured. When the execution button 501 on the control software screen is pressed, the anterior segment image is displayed on the anterior segment monitor 512. When a center of a pupil is not correctly displayed on the screen center, first, the head unit 102 is moved to a roughly correct position by using the joystick 107. When further adjustment is necessary, the jaw receiver driving unit 109 is finely moved by pressing the electric stage button 503 on the control screen.

In step S803, a WFSLO image is captured. When the anterior segment image is displayed roughly in a correct state, the WFSLO image is displayed on the WFSLO monitor 515. The fixation lamp is set in a center position by the fixation lamp position monitor 513, and guided around a line of sight of the subject's eye 207.

Then, watching the WFSLO intensity monitor 516, the focus adjustment button 504 is adjusted to increase the WFSLO intensity. On the WFSLO intensity monitor 516, the signal intensity detected by the WFSLO unit is time-sequentially displayed with a horizontal axis indicating time and a vertical axis indicating the signal intensity. By adjusting the focus adjustment button 504, the positions of the lenses 125-10, 235-14, 235-16, and 235-18 are simultaneously adjusted.

When the WFSLO image is clearly displayed, the WFSLO recording button 517 is pressed to store WFSLO data.

In step S804, first focus adjustment is performed. The subject can adjust a focus while watching the WFSLO image. In this step, based on the WFSLO image displayed on the WFSLO monitor 515 or the information of the intensity displayed on the WFSLO intensity monitor, the subject adjusts the focus so that the image can be clearer or the intensity can be larger. The adjustment is performed by pressing the focus adjustment button 504. By pressing the focus adjustment button 504, the focuses of the AOSLO, the beacon light (measuring light), and the fixation lamp can be simultaneously adjusted interlockingly.

If the control PC 106 executes control for automatically adjusting the position of the focus lens based on the WFSLO image, adjustment time and labor can be reduced, and quick imaging can be performed.

In step S805, an AOSLO image acquisition position is determined. The displayed WFSLO image is confirmed, and a position for acquiring an AOSLO image is determined by a unit described below. Then, the line of sight of the subject's eye 207 is guided so that the position can be set on the center of the WFSLO monitor 515.

There are two methods for determining an acquisition position of the AOSLO image: one is a method for instructing a position of the fixation lamp on the fixation lamp monitor 513, and the other is a method for clicking a desired position on the WFSLO monitor 515. A pixel on the WFSLO monitor 515 and the position of the fixation lamp are associated with each other. The position of the fixation lamp is automatically moved, and the line of sight can be guided to a desired position.

After confirmation that the acquisition position of the AOSLO image has moved to the center on the WFSLO monitor 515, the processing proceeds to a next step.

In step S806, a focus is adjusted base on a defocus value. When the aberration measurement button 506 is pressed, the imaging light 206-2, which is a WFSLO imaging light, is blocked out, and the shutter of the beacon light is opened to radiate the measuring light 206-3, which is beacon light, to the subject's eye 207. A Hartman image detected by the wavefront sensor 255 is displayed on the wavefront sensor monitor 514. Aberration calculated from the Harman image is displayed on the aberration correction monitor 511. The aberration is divided into a defocus component ($\mu$) and all aberration amounts ($\mu$m RMS) to be displayed. Since the positions of the focus lenses 235-10 and 235-16 of the AOSLO imaging light and the beacon light have been adjusted in step S803, preparation has been made for aberration measurement at this step. Specifically, the return light 208 of the measuring light 206-3 passes through the pinhole 298 without being kicked off to reach the wavefront sensor 255.

When the autofocus button 521 is pressed, the positions of the lenses 235-10, 235-14, 235-16, and 235-18 are automatically adjusted so that the defocus value can be reduced.

In step S807, aberration correction is performed. Then, when the aberration correction button 522 is pressed, the spatial light modulator 259 is automatically adjusted in a direction where an aberration amount is smaller, and a value of the aberration amount is displayed in real time. When the value of the aberration amount is equal to or lower than a predetermined threshold value (0.03 $\mu$m RMS), the AOSLO measurement button 507 is automatically pressed, and the processing proceeds to a next step. The threshold value of the aberration amount can be arbitrarily set. When the value of the aberration amount is not equal to or lower than the predetermined threshold value, the aberration correction temporary stop button 508 is pressed to stop the aberration correction. Then, the processing proceeds to a next step by pressing the AOSLO measurement button 507.

In step S808, changing of a focus position of the AOSLO is determined. The focus control instruction acquisition unit 402 determines whether changing of the focus position of the AOSLO independently of the positions of the other focus lenses has been instructed via the operation acquisition unit 401. This is a step for adjusting the imaging position of the AOSLO in a depth direction. For example, if it has acquired an input indicating pressing of a depth adjustment button 524, the focus control instruction acquisition unit 402 determines that changing of the focus position of the AOSLO independently has been instructed. When it has been instructed (YES In step S808), the processing proceeds to step S809, and to step S810 when not (NO in step S808).

In step S809, the focus position of the AOSLO is changed. The focus position control unit 406 adjusts the focus of the AOSLO according to the instruction (first instruction) of adjusting the focus lens 235-10 of the AOSLO separately from the other focus lenses.

In step S810, an AOSLO image is acquired. When the AOSLO measurement button 507 is pressed, the measuring light 206-3 that is beacon light is blocked out, and the shutter of the AOSLO imaging light 206-1 is opened to radiate the imaging light 206-1 to the subject's eye 207. An aberration-corrected AOSLO image is displayed on the AOSLO monitor 518. On the AOSLO intensity monitor 519, as in the case of the WFSLO intensity monitor 516, the signal intensity detected by the AOSLO is time-sequentially displayed.

When the signal intensity is insufficient, watching the AOSLO intensity monitor 519, a focus and a jaw reception position are adjusted to increase the signal intensity.

By the operation condition setting button 523, an imaging field angle, a frame rate, and imaging time can be designated.

By adjusting the depth adjustment button 524 to move the lens 235-10, an imaging range of the subject's eye 207 in the depth direction can be adjusted. Specifically, an image of a desired layer such as a stratum neuroepitheliale retinae, a nerve fiber layer or a pigmented layer can be acquired.

When the AOSLO image is clearly displayed, the AOSLO recording button 520 is pressed to store AOSLO data. Then, the imaging light 206-1 is blocked out.

In step S811, a next operation is selected. The processing returns to step S805 when the imaging position is changed, and to step S802 when the left and right eyes are switched. To end the imaging, the processing proceeds to a next step.

In step S812, the processing is ended. When the stop button 502 is pressed, the control software terminates.

Figure 9:
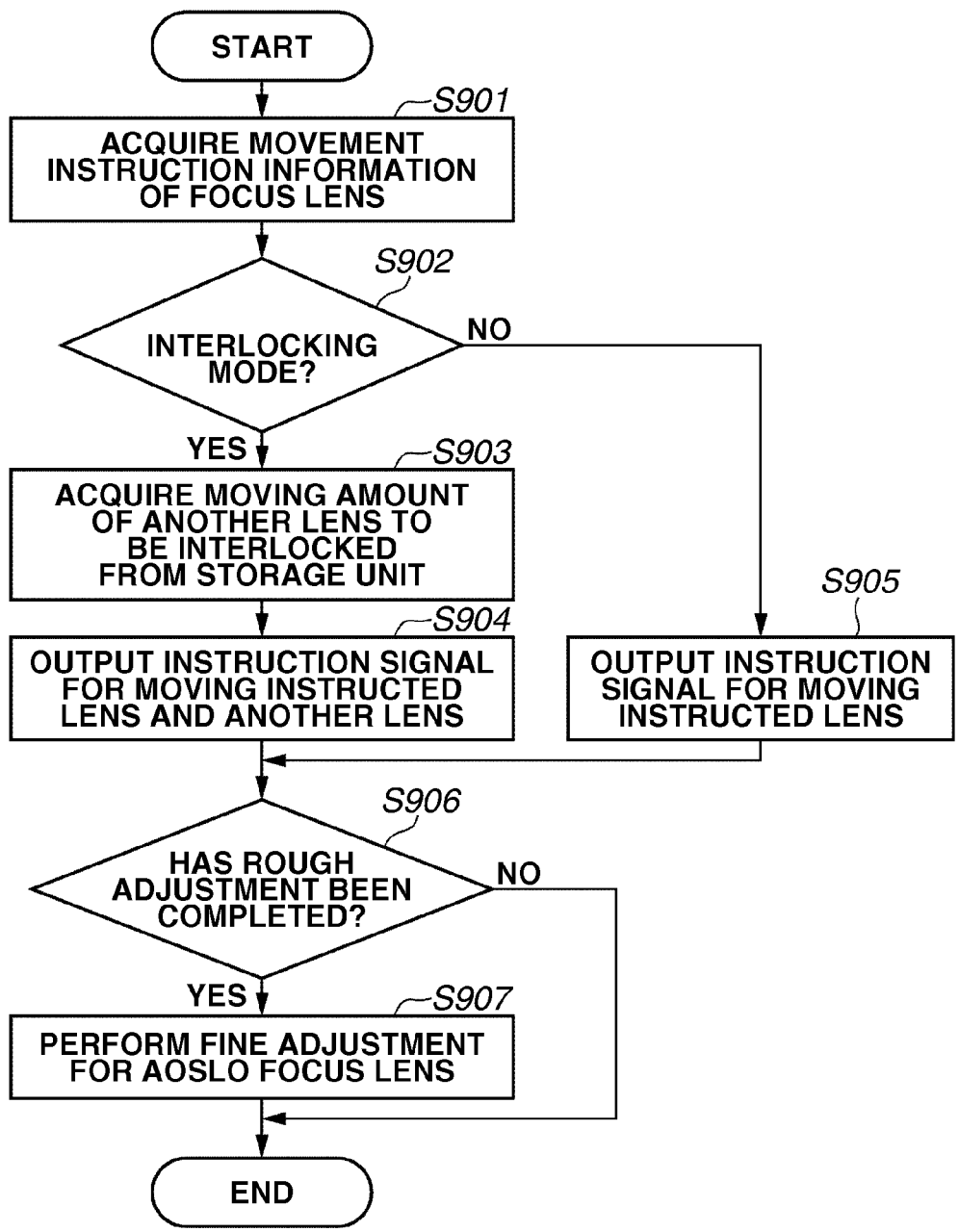
FIG. 9 is a flowchart illustrating control for interlocking of a focus lens according to the exemplary embodiment.

Referring to FIG. 9, adjustment control of a focus lens according to another exemplary embodiment will be described. This control is performed with the configuration illustrated in FIG. 4.

In step S901, the focus control instruction acquisition unit 402 acquires an operation input from the operation unit 451 acquired via the operation acquisition unit 401 or a focus control instruction from an automatic adjustment function. Information about the focus control instruction indicates in which direction and how much the focus lens is moved. Information indicating which of individual control of only the instructed focus lens and interlocking of all the other focus lenses is performed is added to the focus control instruction. Further, information designating focus lenses to be interlocked can be added.

In step S902, the interlocking determination unit 405 determines which of an interlocking mode of interlocking the focus lenses and individual adjustment is performed is performed. This determination is made by referring to the information added to the control instruction. The processing proceeds to step S903 when the interlocking mode is determined (YES in step S902), and to step S905 when not (NO in step S902).

In step S903, the interlocking determination unit 405 selects focus lenses to be interlocked. In the case of setting where all the focus lenses are interlocked, all the focus lenses are selected. When there is added to the additional information of the control instruction information designating focus lenses to be interlocked, only the focus lenses of the information are interlocked.

In step S904, the focus position control unit 406 calculates a moving amount of the focus lens to be interlocked by referring to the information in the storage unit 407. Then, the focus position control unit 406 outputs an instruction signal for moving the lens of the control instruction and the other lenses to be interlocked to the focus driver 283 of the driver unit.

In step S905, the focus position control unit 406 outputs an instruction signal for moving the position of the lens of the control instruction by a moving amount and a moving direction included in the control instruction to the focus driver 283.

In step S906, the control PC 106 determines whether rough adjustment has been completed for the focus lens corresponding to the instruction signal transmitted in step S904 or S905. This processing is for determining, for example, which of ongoing searching for a focusing position of the focus lens and a searching end for the rough adjustment the state is. When it is determined that the rough adjustment has been completed (YES in step S906), then, fine adjustment may be necessary. For example, even when a plurality of lenses is interlockingly controlled, one of the lenses may not be in an appropriate position. Especially, the focus lens of the AOSLO must be positioned with accuracy higher than that of the other focus lenses. In such a case, the control PC 106 outputs an instruction of starting fine adjustment, and auto-focusing is started by using, for example, image information. On the other hand, when an instruction signal of moving the focus lens during the rough adjustment (NO in step S906), there is no need to start fine adjustment. Thus, the processing is ended without proceeding to step S907.

In this step, in addition to the determination as to the end of the rough adjustment, the control PC 106 determines whether fine adjustment is necessary. The information acquisition unit 403 acquires an AOSLO or WFSLO image, a fixation lamp image, or Hartman image by a beacon image, and determines whether further adjustment is necessary by acquiring a luminance value or contrast of an image, or a statistical value of luminance values. For example, irrespective of automatic or manual, even when focus adjustment is performed based on the WFSLO image or when rough adjustment of the focus of the WFSLO has been completed, there is a possibility that a focus of the beacon light to be interlocked may not be appropriate. In such a case, further fine adjustment is performed only for the focus of the beacon light.

In step S907, fine adjustment of the focus lens is performed. For example, in the case of automatic adjustment, a more appropriate focusing position can be acquired by reducing a searching width of the focusing position of the focus lens more than that of the rough adjustment before the fine adjustment.

Figure 10:
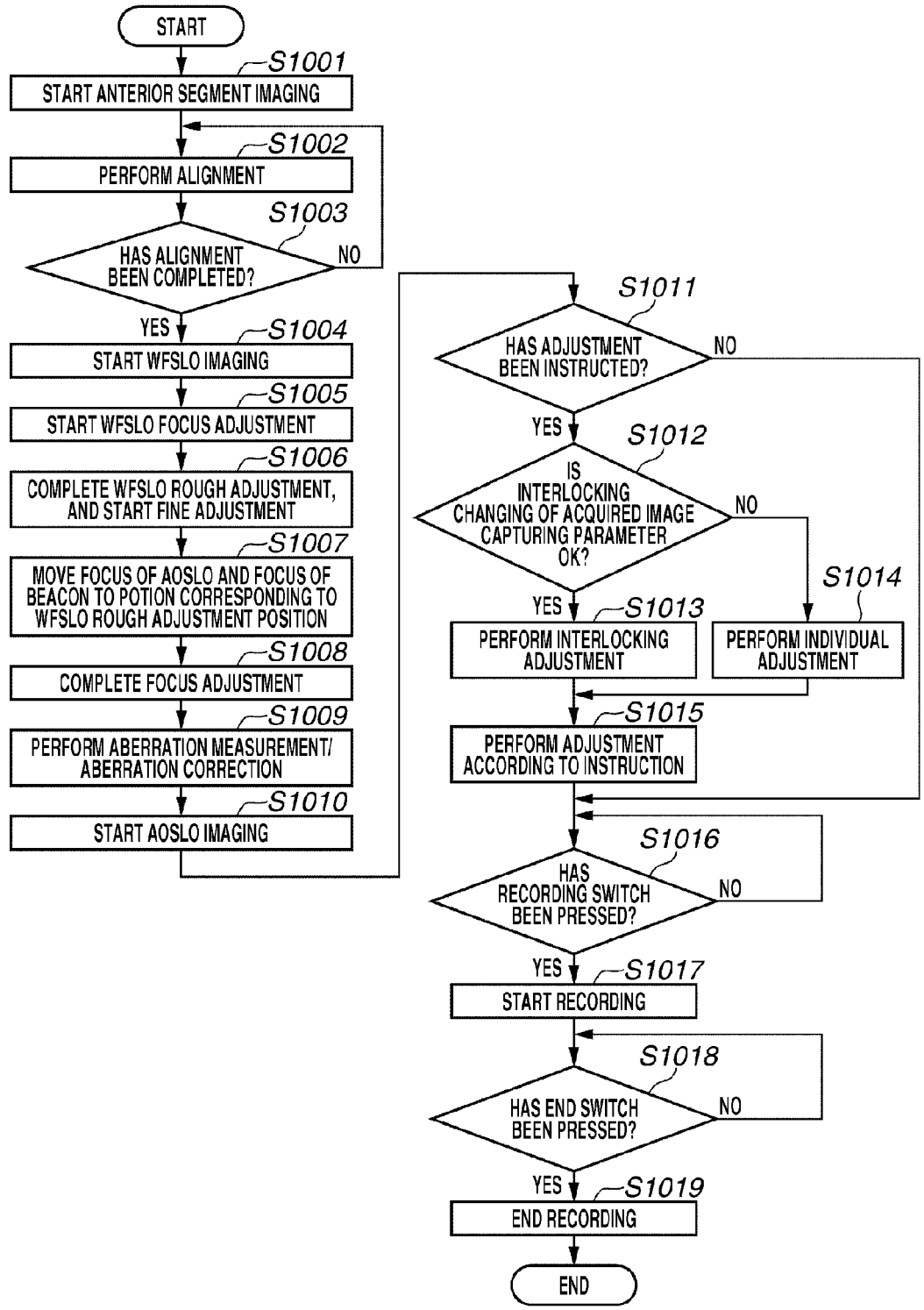
FIG. 10 is a flowchart illustrating a flow of control according to the exemplary embodiment.

Referring to FIG. 10, a flow of imaging control by the AOSLO according to the other exemplary embodiment will be described. A main unit of the imaging control is the control PC 106. In the present exemplary embodiment, various adjustment operations such as focus adjustment are automatically performed.

In step S1001, the light source 201-4 is lit, the detector 260 starts imaging driving, and an acquired moving image is displayed on the anterior segment monitor 512. Imaging can be started according to, for example, rough alignment of the jaw receiver 104 or the head unit 102, or an operation input indicating pressing of the start button 501.

In step S1002, alignment is started. The alignment, which can be adjusted manually by pressing the electric stage button 503, is automatically performed by analyzing an image of the anterior segment via the control PC 106 and controlling the head unit 102 so that a pupil size and a position can be appropriate. Start timing of the auto-alignment can be manually instructed. However, for example, if the alignment is started according to detection of the pupil in the anterior segment image, adjustment time and labor can be reduced.

In step S1003, the control PC 106 determines whether the alignment has been completed. For example, the control PC 106 determines whether the pupil position is shifted from a reference position or whether a size is shifted from a reference by imager analysis. When it is determined that the alignment has not been completed (NO in step S1003), the processing proceeds to step S1002 to perform adjustment again. When it is determined that the alignment has been completed (YES in step S1003), the processing proceeds to step S1004.

Thereafter, if the control PC 106 continuously monitors the image of the anterior segment and performs anterior segment tracking processing for changing the position of the head unit 102 following movement of the anterior segment, the control PC 106 can deal with positional deviation between the fundus and the head unit 102 after the alignment.

In step S1004, WFSLO imaging is started according to the alignment completion. The shutter of the light source 201-2 of the imaging light 206-2 is opened, the scanner 219-2 is driven, and the detector 238-2 starts imaging. An image acquired by the detector 238-2 is displayed on the WFSLO monitor 515 of the liquid crystal monitor 105 by the display control unit 408.

Imaging start timing of the WFSLO can be before the completion of the alignment. For example, when the alignment is adjusted at two stages, i.e., rough adjustment and fine adjustment, imaging of the WFSLO can be started at completion timing of the rough adjustment. When the imaging start timing of the WFSLO is faster, entire adjustment time can be shortened.

In step S1005, focus adjustment for focusing the focus lens 235-14 of the WFSLO on the fundus is started. The focus adjustment is started roughly simultaneously with the imaging start of the WFSLO in step S1004. Processing for specifying a focusing position of the focus lens of the WFSLO is performed by the focus position specifying unit 404 based on image information or an output from the dedicated focus sensor.

In step S1006, the rough adjustment of the focus lens 235-14 of the WFSLO is completed to start fine adjustment. For the focus adjustment started in step S1005, when two-stage adjustment, i.e., the rough adjustment and the fine adjustment, is not performed, step S1006 can be omitted.

In step S1007, the control PC 106 starts control for moving the focus of the AOSLO and the beacon light (measuring light) to a position corresponding to the rough adjustment position of the WFSLO according to the start of the fine adjustment. In this step, processing for focusing measuring light for measuring aberration on the object is performed by controlling a state of the focus lens 235-16. Processing for focusing imaging light of the AOSLO for capturing an image of the object on the object is performed by controlling a state of the focus lens 235-10 interlockingly with the control of the state of the focus lens 235-16.

Needless to say, a focus of the fixation lamp can be controlled simultaneously. Thus, there is no need to always interlock the plurality of focus lenses simultaneously. The other focus lenses can be interlocked with a time difference after completion of rough adjustment of one focus lens. According to this control, for example, when the focus lens is moved to search for a focusing position, the focus lenses are interlocked with a delay at the completion timing of the rough adjustment because interlocking for the searching movement is useless. The focus lenses can be interlocked at timing when the processing up to the fine adjustment is completed and a focusing position is finally determined.

In step S1008, the focus position control unit 406 completes the focus adjustment of the WFSLO, and interlockingly completes the focus adjustment of the AOSLO, the beacon light (measuring light), and the fixation lamp.

In step S109, the wavefront sensor 255 starts formation of a Hartman image. The control PC 106 acquires the acquired Hartman image. The display control unit 407 displays the Harman image on the wavefront sensor monitor 514 of the liquid crystal monitor 105. Further, the wavefront sensor 255 sequentially calculates aberration for the acquired Harman image. The control PC 106 acquires the calculated aberration. The display control unit 407 displays the calculated aberration on the aberration correction monitor 511 of the liquid crystal monitor 105. In response to outputting of the calculated aberration value, the control PC 106 changes the state of the spatial light modulator 259 via the spatial light modulator driver 288 in the driver unit 281. The control PC 106 controls a phase difference generated by the spatial light modulator 259 to reduce the calculated aberration.

The control of the spatial light modulator is performed corresponding to, among the calculated aberrations, an item other than a defocus item. The defocus item is compensated for by changing the position of the focus lens. The focus position control unit 406 changes the position of the AOSLO focus lens 235-10 according to a defocus value. The focus position control unit 406 interlocks the focus lens 235-16 of the beacon light (measuring light) with the position of the AOSLO focus lens 235-10.

To start AOSLO imaging in step S1010, the shutter for blocking out the light of the light source 201-1 of the imaging light 206-1 is opened, the scanner 219-1 is driven, and the detector 238-1 starts imaging driving. Accordingly, an image of the object is captured by return light of the imaging light 206-1 passed through the spatial light modulator 259 and the focus lens 235-10. Imaging start timing of the AOSLO can be before or after the start of aberration measurement and correction.

The processing of steps S1011 to S1015 is manual adjustment performed according to an inspector's wish in addition to the autofocus control. The focus control instruction acquisition unit 402 determines whether a focus control instruction has been acquired. The processing proceeds to step S1016 when there is no instruction (NO in step S1011). The processing proceeds to step S1012 when there is an instruction (YES in step S1011).

In step S1012, the interlocking determination unit 405 determines whether the control instruction received in step S1011 is an instruction to perform individual movement of only one focus position independently of the other focus lenses. For example, the interlocking determination unit 405 determines this based on which of a control instruction by pressing of the focus adjustment button 504 and a control instruction by pressing of the depth adjustment button 524 the instruction is. When it is determined that interlocking is performed (YES in step S1012), in step S1013, interlocking adjustment is performed for the plurality of focus lenses. When it is determined that interlocking is not performed (NO in step S1012), in step S1014, individual adjustment is performed.

Especially, the processing of individually controlling the AOSLO focus positions to move them to target imaging positions (in the depth direction) can be automatically performed. For example, when an imaging position is determined for the purpose of observing a visual cell, the interlocking determination unit 405 determines whether a peak appears in a specific frequency component corresponding to a repeated pattern of the visual cell for a frequency image of the AOSLO image. The camera can be automatically focused on a position for acquiring a visual cell image by performing the determination while moving the focus position of the AOSLO. In addition, the focus can be automatically adjusted by determining appearance of a characteristic pattern of the target imaging position. Further, a rough position of the fundus taking a working distance or an axial length into consideration can be understood based on a focusing position of the beacon light (measuring light) or the WFSLO. Thus, to capture an image of a choroid membrane side, the camera is focused on a position deep by an experimentally calculated specific value (first value). To capture an image of a vitreous body side, the camera is focused on a position shallow by an experimentally calculated specific value (second value). Thus, by controlling the state of the focus lens 235-10 according to the imaging position of the object in the depth direction, the focus of the AOSLO can be automatically adjusted in the target imaging position or a position near it.

In step S1016, the operation acquisition unit 401 stands by until pressing of the AOSLO recording button 520 is input. When it is determined that the recoding button has not been pressed (NO in step S1016), standing-by for the manual adjustment instruction of step S1011 and standing-by for a recording instruction are repeated. When an AOSLO image having aberration reduced equal to or lower than a reference value is acquired, recording is automatically started under control of the control PC 106, and thus a high-definition fundus image can be easily acquired. As another example, processing of constantly recording AOSLO images and deleting the recorded AOSLO images during periods other than an instructed period can be applied. This can reduce a possibility that even if the AOSLO images having aberration sufficiently reduced have been captured, they cannot be recorded without any recording instruction.

In step S1017, the control PC 106 starts recording according to a recording start instruction.

In step S1018, the control PC 106 waits for a recording end instruction. The recording end instruction is issued in response to pressing of the AOSLO recording button 520 again in a pressed and recording state of the AOSLO recording button 520. In step S1019, the control PC 106 ends the recording according to the recording end instruction.

Figure 11:
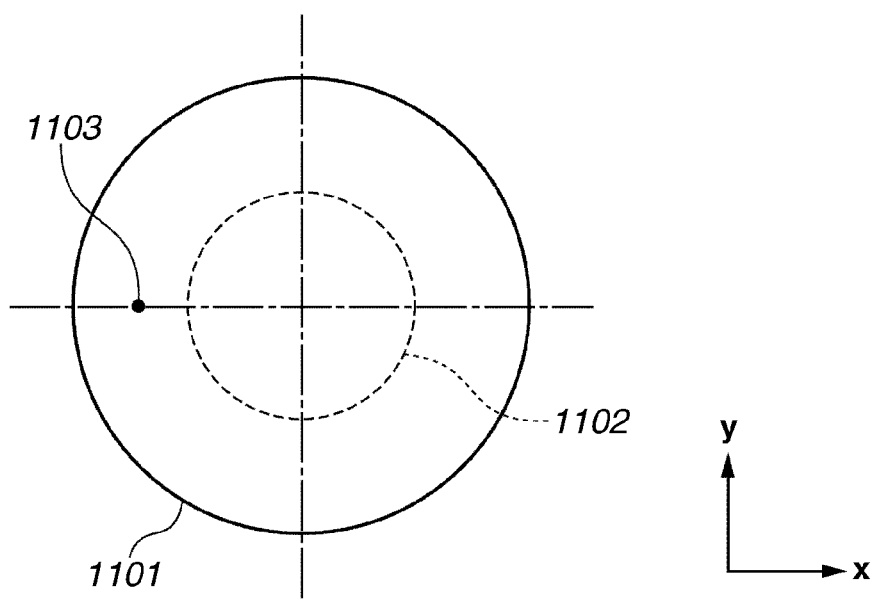
FIG. 11 illustrates an incident position of measuring light to a pupil.

Referring to FIG. 11, an incident position of the beacon light (measuring light) on the pupil will be described. FIG. 11 illustrates the incident position of the measuring light 206-3 when the anterior segment of the subject's eye (xy section of the anterior segment) is seen from a visual axis (Z axis). In many cases, the pupil 1101 has a circular shape of about φ 4 mm under normal brightness while it varies from individual to individual. The incident position 1103 is an incident position of each illumination light, indicating that the measuring light is condensed near the pupil. A region surrounded with a broken-line circle is an effective pupil 1102 of the imaging optical system, which is φ 2 mm on the pupil.

The incident position 1103 of the illumination light is set so that the illumination light can enter outside a range of the pupil 1102 of the imaging optical system in the pupil 1101. Each is separated by 1.5 mm from the visual axis. Thus, by dividing the pupil between the measuring light optical system and the imaging optical system, a reflected light from a cornea surface can be removed.

In the present exemplary embodiment, a region on a retina illuminated with the imaging light is about φ 9 mm. However, when the beam intensity has Gaussian distribution, the light must be condensed up to several won the pupil to secure brightness uniformity in an imaging region. For example, to secure the intensity of a surrounding portion relative to a center of the irradiation region of φ 9 mm up to 60%, a spot diameter of about 3.5 μm on the pupil is necessary.

When brightness of a captured image is sufficiently secured only by one illumination light, energy per area on the pupil increases. When light of a near infrared wavelength is used, there is a possibility that the energy will change into heat to apply a burden on an organ such as a cornea or a crystal lens. To prevent such a burden, in the present exemplary embodiment, the imaging light and the measuring light are made to enter the separate positions on the pupil. Thus, without increasing burdens on the subject's eye, a double amount of illumination light to the retina can be secured.

In the present exemplary embodiment, the number of measuring light beams is one. However, the number of measuring light sources can be increased. When more measuring light beams enter, by an amount of each measuring light beam, image brightness can be increased four times without increasing burdens on the anterior segment. Thus, a further improvement of the image quality can be expected.

When a mechanism enabling individual setting of an amount of each measuring light beam is provided, and the anterior segment of the subject's eye is partly clouded due to a disease, a loss of an amount of illumination light to the retina can be prevented. For example, when an amount of each measuring light beam is normally set low, a clouded spot is present near the incident position 1103 of the measuring light, and beam's efficiency of reaching the retina decreases, the beam is switched OFF at the incident position 11033. Then, the amounts of beams at the other incident positions are increased. Accordingly, a bright image can be secured without reducing the amount of beam to illuminate the retina.

When a light source such as a semiconductor laser higher in coherence than natural emitted light is used as a measuring light source, speckle noise is generated due to roughness of the retina surface. On the other hand, in the present exemplary embodiment, such speckle noise can be reduced by superimposing illumination light beams from a plurality of light sources on the retina. If there is no correlation between spackle patterns of a captured image caused by the illumination light beams, speckle contrast can be reduced by $1/\sqrt{4}$ times. It is difficult to completely eliminate correlation. However, according to the present exemplary embodiment, the incident angles of the illumination light beams to the retina are different from one another. Thus, by setting polarization of the illumination light beams different in addition to this, the correlation can be reduced, and thus speckle contrast can be reduced.

Figure 12:
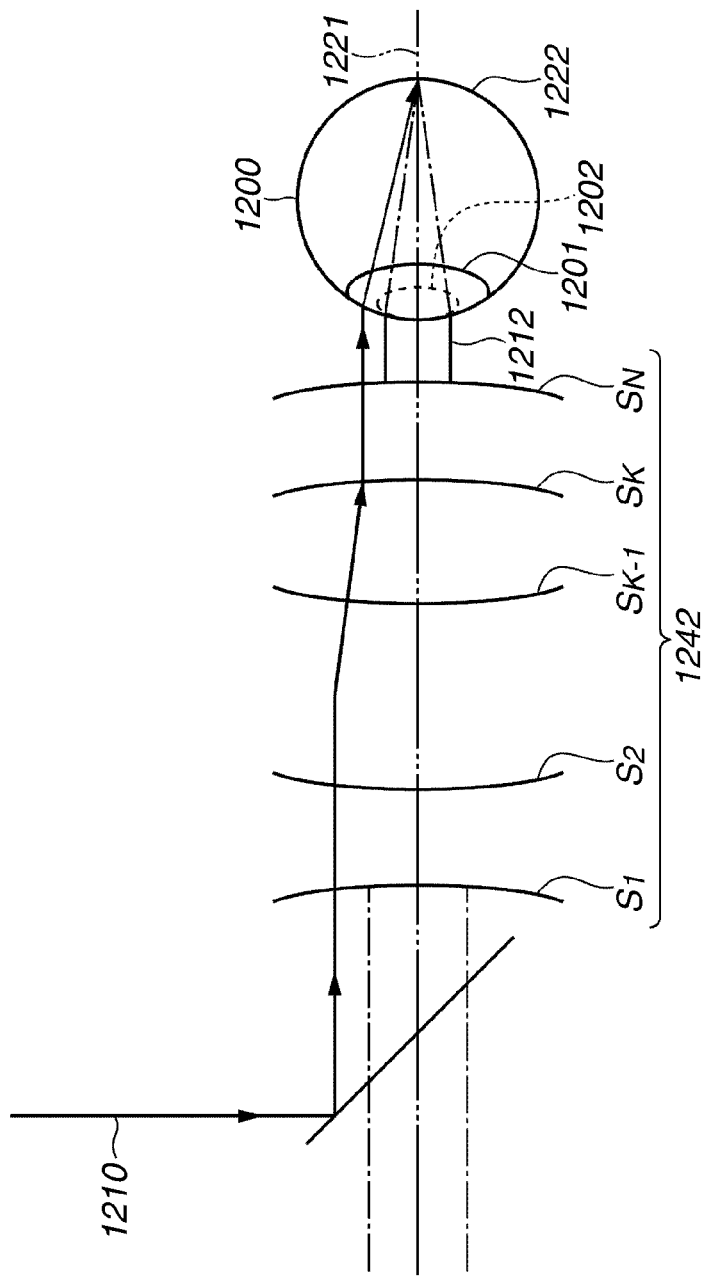
FIG. 12 illustrates a configuration of an optical system for guiding the measuring light to the pupil.

Referring to FIG. 12, an optical system for shifting the beacon light (measuring light) from the pupil center to enter will be described.

Apart of the optical system through which the return light of the beacon light and the imaging light pass is configured as illustrated in FIG. 12. A light flux (principal ray thereof) 1210 of the measuring light (beacon) 206-3 from the measuring light source enters a perforated mirror having a function of limiting the return light from the retina to be reflected on its mirror portion. A hole of the perforated mirror, which is set with an angle according to an optical axis of a common portion of first and second optical systems, is illustrated without being tilted to be easily viewed in FIG. 12. The reflected light 1210 enters a pupil 1201 of an eye ball 1200 via an eyepiece optical system 1242 including lens surfaces S1 to SN to illuminate the retinal 1222 in a line shape. Reflected/backscattered light 1212 from the retina 12 is conversely output from the pupil 120, and passes through the hole of the perforated mirror via the eyepiece optical system 1242 to form an image on the wavefront sensor 255 by the image forming optical system 1242.

The combinations of the exemplary embodiments are within the present invention. For example, as an example of the focusing unit, the focus lens movable along the optical axis has been used. However, a mirror can be used to adjust an in-focus state. The information indicating the state of the focusing unit can be a position of the focus lens in the optical axis or a state of the mirror for adjusting an in-focus state.

An exemplary embodiment where a part of the present invention is realized by cooperation of a program with hardware is also within the invention. According to the exemplary embodiment of the program, a program corresponding to the processing illustrated in FIGS. 8 to 10 and a program corresponding to the display surface illustrated in FIGS. 5 and 6 are stored in the storage unit 407, and the CPU of the control PC 106 loads the programs into the RAM to execute commands included in the programs.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-126196 filed Jun. 1, 2012, which is hereby incorporated by reference herein in its entirety.

What is claimed is:

1. An imaging apparatus comprising:
a measuring light focusing unit configured to focus measuring light for measuring aberration of an object on the object;
an aberration correction unit configured to change a state based on the aberration measured with the measuring light;
an imaging light focusing unit configured to focus imaging light for capturing an image of the object on the object;
an imaging unit configured to capture an image of the object with the imaging light having passed through the aberration correction unit and the imaging light focusing unit; and
a control unit configured to interlockingly control states of the measuring light focusing unit and the imaging light focusing unit.

2. The imaging apparatus according to claim 1, further comprising an aberration measurement unit configured to measure the aberration based on return light of the focused measuring light from the object,
wherein the control unit controls a state of the imaging light focusing unit according to a state of the measuring light focusing unit, and controls the state of the imaging light focusing unit based on a defocus value measured by the aberration measurement unit.

3. The imaging apparatus according to claim 1, further comprising an instruction unit configured to control a state of the imaging light focusing unit independently of a state of the measuring light focusing unit,
wherein the control unit controls the state of the imaging light focusing unit according to an instruction from the instruction unit.

4. The imaging apparatus according to claim 3, further comprising a display control unit configured to display an image captured by the imaging unit on a display unit,
wherein the instruction unit includes a button displayed on the display unit by the display control unit.

5. The imaging apparatus according to claim 1, further comprising:
a first instruction unit configured to control a state of the imaging light focusing unit independently of a state of the measuring light focusing unit; and
a second instruction unit configured to interlockingly control the states of the imaging light focusing unit and the measuring light focusing unit,
wherein the control unit controls the state of the imaging light focusing unit according to instructions from the first and second instruction units.

6. The imaging apparatus according to claim 1, further comprising:
a second imaging light focusing unit configured to focus second imaging light different from the imaging light on the object; and
a second imaging unit configured to capture an image having a field angle wider than that of the image based on the second imaging light,
wherein the control unit interlockingly controls the states of the second imaging light focusing unit, the measuring light focusing unit, and the imaging light focusing unit.

7. The imaging apparatus according to claim 6, further comprising:
a first instruction unit configured to control the state of the imaging light focusing unit independently of the states of the measuring light focusing unit and the another imaging light focusing unit; and
a second instruction unit configured to interlockingly control the states of the imaging light focusing unit, the measuring light focusing unit, and the second imaging light focusing unit,
wherein the control unit controls the state of the imaging light focusing unit according to instructions from the first and second instruction units.

8. The imaging apparatus according to claim 5, further comprising a display control unit configured to display an image captured by the imaging unit on a display unit,
wherein the first and second instruction units include buttons displayed on the display unit by the display control unit.

9. The imaging apparatus according to claim 1, wherein the control unit further controls the state of the imaging light focusing unit according to an imaging position of the object in a depth direction.

10. The imaging apparatus according to claim 1, wherein the object includes an eye of a subject.

11. The imaging apparatus according to claim 10, further comprising:
   a fixation lamp display unit configured to display a fixation lamp watched by the eye; and
   a fixation lamp focusing unit configured to focus light from the fixation lamp on the eye,
   wherein the control unit interlockingly controls the states of the measuring light focusing unit and the fixation lamp focusing unit.

12. The imaging apparatus according to claim 10, further comprising:
   an optical system configured to cause the measuring light to enter by shifting the light from a pupil center of the eye;
   a pinhole configured to block out a part of return light of the measuring light having passed through the optical system and the measuring light focusing unit from the eye;
   a detection unit configured to detect the return light having passed through the pinhole; and
   an aberration measurement unit configured to measure the aberration based on the detected return light.

13. The imaging apparatus according to claim 10, wherein the optical system causes the measuring light to enter from outside a range of an effective pupil of the imaging light in the eye.

14. The imaging apparatus according to claim 10, wherein the pinhole is disposed to be conjugate with a fundus of the eye.

15. The imaging apparatus according to claim 1, wherein the measuring light focusing unit includes a measuring light focusing lens movable along an optical axis of an optical path of the measuring light,
   wherein the imaging light focusing unit includes an imaging light focusing lens movable along an optical axis of an optical path of the imaging light, and
   wherein the control unit interlockingly moves the measuring light focusing lens and the imaging light focusing lens.

16. An imaging apparatus for capturing an image of a subject's eye with imaging light having passed through an aberration correction unit adjusted according to aberration of the subject's eye, the imaging apparatus comprising:
   an imaging light focusing unit configured to focus the imaging light for capturing the image of the subject's eye on the subject's eye;
   a measuring light focusing unit configured to focus measuring light for measuring the aberration on the subject's eye; and
   a control unit configured to interlockingly control states of the measuring light focusing unit and the imaging light focusing unit.

17. An imaging apparatus comprising:
   a measuring light focusing unit configured to focus measuring light for measuring aberration on a subject's eye;
   an optical system configured to cause the measuring light to enter by shifting the light from a pupil center of the subject's eye;
   a pinhole configured to block out a part of return light of the measuring light from an object;
   a detection unit configured to detect the return light having passed through the pinhole; and
   an aberration measurement unit configured to measure the aberration based on the detected return light.

18. A method for controlling an imaging apparatus, the method comprising:
   focusing measuring light for measuring aberration on an object by controlling a state of a measuring light focusing unit;
   focusing imaging light for capturing an image of the object on the object by controlling a state of an imaging light focusing unit interlockingly with control of the measuring light focusing unit;
   changing a state of an aberration correction unit based on the aberration measured with the measuring light; and
   capturing the image of the object with the imaging light having passed through the aberration correction unit and the imaging light focusing unit.

19. A control method comprising:
   focusing measuring light for measuring aberration on an object by controlling a state of a measuring light focusing unit;
   focusing imaging light for capturing an image of the object on the object by controlling a state of an imaging light focusing unit interlockingly with control of the measuring light focusing unit;
   measuring the aberration based on the measuring light having passed through the measuring light focusing unit;
   controlling a state of the imaging light focusing unit based on a defocus value acquired from the measured aberration; and
   controlling the state of the imaging light focusing unit according to an imaging position of the object in a depth direction.

20. A non-transitory computer-readable storage medium storing a program that cause a computer to execute the method according to claim 18.

* * * * *